United States Patent [19]

Nakanishi et al.

[11] Patent Number: 4,776,687
[45] Date of Patent: Oct. 11, 1988

[54] APPARATUS FOR DETECTING OPHTHALMIC DISEASE

[75] Inventors: Takaji Nakanishi, Tokyokawa; Koichiro Kakizawa, Okazaki; Nobuyuki Yasuda; Shinichiro Shinoda, both of Gamagouri, all of Japan

[73] Assignee: Kowa Company, Ltd., Japan

[21] Appl. No.: 98,497

[22] Filed: Sep. 18, 1987

Related U.S. Application Data

[63] Continuation of Ser. No. 743,567, Jun. 11, 1985, abandoned.

[51] Int. Cl.$^4$ .............................................. A61B 3/10
[52] U.S. Cl. ...................... 351/214; 351/205; 351/221
[58] Field of Search .................... 351/205, 214, 221

[56] References Cited

U.S. PATENT DOCUMENTS

| | | | |
|---|---|---|---|
| 3,703,176 | 11/1972 | Vassiliadis | 351/221 X |
| 3,783,874 | 1/1974 | Koester | 351/221 X |
| 4,208,107 | 6/1980 | Oharek | 351/221 X |
| 4,477,159 | 10/1984 | Mizuno | 351/221 |
| 4,582,405 | 4/1986 | Muller et al. | 351/221 |

Primary Examiner—Rodney B. Bovernick
Attorney, Agent, or Firm—Ralph R. Rath

[57] ABSTRACT

An apparatus for detecting ophthalmic disease such as a cataract in the lens of a patient's eye includes means for focussing a laser beam and slit light alternatively or simultaneously at a selected spot in the lens of the eye. The slit light is used in a monitoring or adjustment mode to illuminate the selected spot and its adjacent portion on which the laser beam is to be focussed for ophthalmic disease detection, thereby making easier the identification of spots to be measured in the lens of the eye.

2 Claims, 3 Drawing Sheets

APPARATUS FOR DETECTING OPHTHALMIC DISEASE

REFERENCE TO RELATED APPLICATION

This application is a Continuation of application Ser. No. 743,567, filed June 11, 1985, now abandoned.

BACKGROUND OF THE INVENTION

1. Field of the Invention

This invention relates to an apparatus for detecting ophthalmic disease in the lens of a patient's eye, and more particularly to an apparatus for detecting turbidity caused by a cataract in the lens of the patient's eye for earlier detection or preparatory prevention thereof.

2. Description of the Prior Art

The cataract, one of the typical ophthalmic diseases, is a disease in which protein particles of the human crystalline lens increase in size to cause it to become turbid. To make an earlier detection or preparatory prevention of the cataract in a medical treatment, it is necessary to measure the size or diameter of the protein particles.

A human eye includes transparent parts such as the cornea, the crystalline lens, etc. Fine protein particles float in these transparent parts and cause a Brownian movement. The protein particles are distributed in the form of small diameter particles in normal disease-free eyes, but in the form of particles of larger diameter in turbid eyes.

In the prior art, the apparatus for measuring the diameter of the protein particles includes a laser to produce a laser beam which is focussed on a selected portion of the crystalline lens of the patient's eye to be measured. The protein particles which make the Brownian movement and pass through the portion in the lens of the eye at which the laser beam is focussed cause the laser beam to be reflected and back-scattered thereon. The thus back-scattered laser beam is partially directed toward the eyepiece of a binocular microscope for monitoring, and partially directed to a photomultiplier to convert the intensity of the back-scattered beam into an electrical signal, which is applied to a correlator to obtain a time correlation for determining how the back-scattered beam fluctuates in intensity in time. The correlation is then used to calculate the relaxation time of intensity of fluctuation of the back-scattered beam and derive therefrom a diffusion coefficient, thereby determining the diameter of the protein particles.

The spot at which the laser beam is focussed is monitored or photoelectrically measured as mentioned above, but not irradiated with illuminating light, so that it is very difficult to identify the measuring spot if it is shifted into another point in an attempt to measure the diameter or protein particles in the crystalline lens of the patient's eye. This requires such time and effort to identify the point or spot to be measured and causes pain to the patient.

SUMMARY OF THE INVENTION

It is therefore an object of the present invention to provide an apparatus for detecting ophthalmic disease in a patient being capable of easily making a preparatory monitoring or adjustment for selected portions in the lens of the eye to be measured.

It is another object of the present invention to provide an apparatus for detecting ophthalmic disease in a patient being capable of being rapidly and easily operated to reduce discomfort to the patient.

In accordance with the present invention, the apparatus for detecting ophthalmic disease in a patient includes means for focussing a laser beam at a selected spot in the lens of a patient's eye and means for focussing slit light on or in proximity to the selected spot thereof. The slit light is focussed on the portion or spot to be measured with or without the focussed laser beam to illuminate the selected portion or spot in the lens of the eye on which the laser beam is focussed.

This arrangement according to the present invention allows preparatory monitoring or adjustment of portions or spots to be measured and the reduction of discomfort to the patient.

BRIEF DESCRIPTION OF THE DRAWINGS

The objects and features of the present invention will become more apparent from a consideration of the following detailed description taken in conjunction with the accompanying drawings in which.

DETAILED DESCRIPTION OF THE PREFERRED EMBODIMENTS

Figure 1:
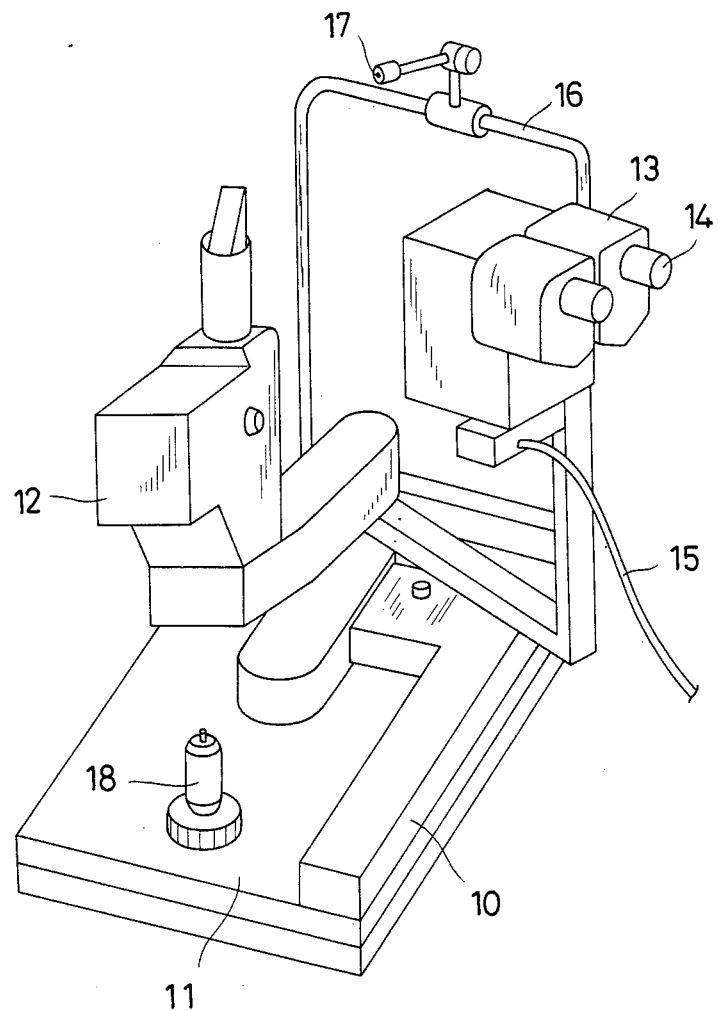
FIG. 1 is a schematic perspective view showing the whole appearance of the apparatus of the present invention.

FIG. 1 shows one embodiment of the apparatus for detecting ophthalmic disease in a patient according to the present invention. In FIG. 1, a laser 10 for producing a laser beam is fixedly mounted on a base plate 11 of the apparatus. The laser beam is focussed at a selected spot in the lens of a patient's eye (not shown), as will be more fully described. The selected spot in the lens of the eye is illuminated by slit light which is produced in a housing 12 in which an optical system for focussing the slit light is accommodated. The light reflected and back-scattered on a portion of the eye is monitored by a binocular microscope arrangement 13 with an eyepiece 14 and also guided to a photomultiplier (not shown) via a fiber optic cable 15 (which can eventually be eliminated). The apparatus also includes a support 16 on which a lamp 17 is adjustably mounted to produce light, which is viewed by the patient during a monitoring or detection mode in order to hold the patient in a stationary position.

The angle of illumination of the slit light or laser beam is adjusted by adjusting housing 12, while the monitoring angle is also adjusted by adjusting the monitoring arrangement.

An input device 18 is provided on base plate 11 to operate a controller (not shown) which controls the power of the laser or light source, the position of a movable mirror and other measuring devices necessary for detecting ophthalmic disease.

Figure 2:
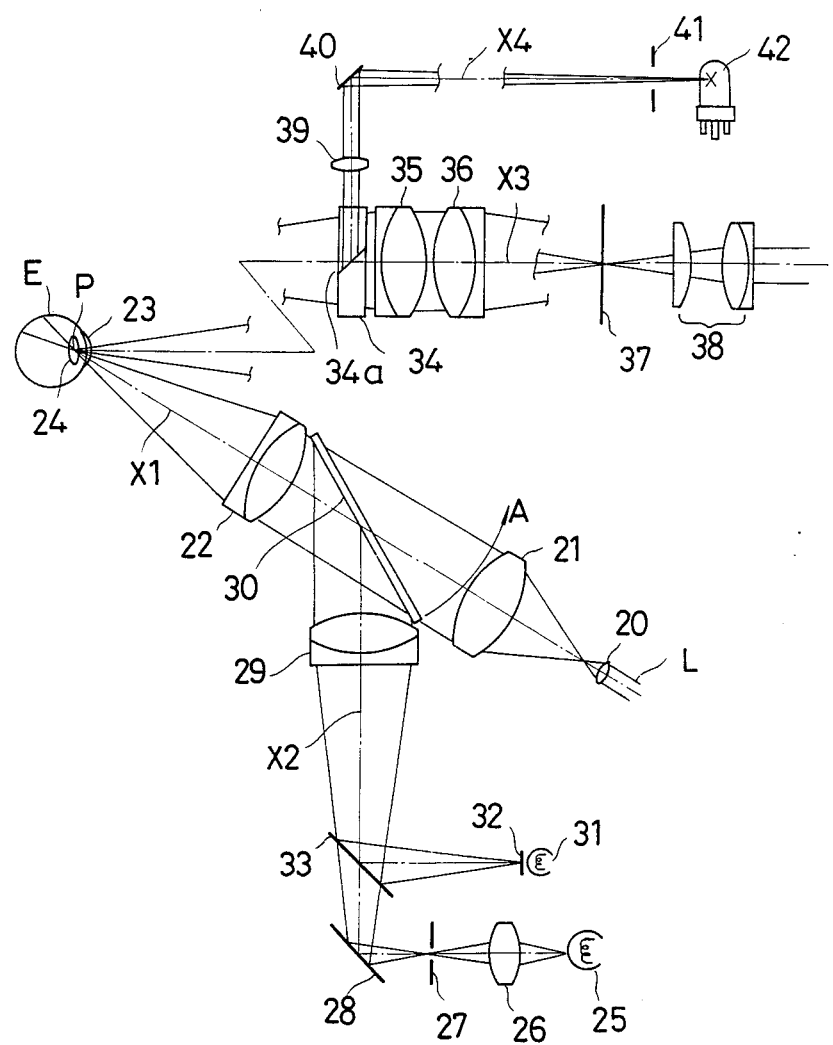
FIG. 2 is a schematic view showing the overall optical arrangement to irradiate the patient's eye with the laser beam and slit light.

FIG. 2 shows one embodiment showing an overall optical arrangement of the present invention, in which a laser beam L from laser 10 is converged by a converging lens 20 and then collimated by a collimating lens 21 arranged on the same optical axis X1 as converging lens 20. The collimated laser beam falls onto a focussing lens 22 which focuses the laser beam at a selected spot P of the patient's eye E including a cornea 23 and a crystalline lens 24 to be measured.

A movable mirror 30 is disposed between focussing lens 22 and collimating lens 21 and mounted to pivot in the direction A out of the optical axis X1 for illumination of the patient's eye with laser beam L. The movable mirror 30 also takes another position as shown in FIG. 2 to define another optical axis X2 on which a collimating lens 29 and a mirror 28 are arranged to guide slit light to focussing lens 22 which focuses slit light to produce a slit image in proximity to selected spot P of the patient's eye. The slit light is produced by a slit 27 illuminated by a light source 25 through a lens 26. On the same optical axis X2 there is also disposed a semi-transparent mirror 33 for directing the light from a pinhole 32 illuminated by a light source 31 toward collimating lens 29 and focussing lens 22 for focussing light from pinhole 32 at spot P in the lens of the eye. This pinhole image serves as a dummy spot image which is replaced by the laser spot during the measuring or detecting mode.

In this optical arrangement, spot P is in a conjugate relation relative to slit 27 with respect to the optical system including focussing lens 22 and collimating lens 29, and also in a conjugate relation relative to pinhole 32 with respect to the same optical system.

A part of the light reflected on a back-scattered from spot P in the cornea 23 of eye E to be measured reaches a beam splitter 34 which splits the back-scattered laser beam into a monitoring arrangement including an objective lens 35 and a focussing lens 36 arranged on an optical axis X3 to focus the back-scattered light on a monitoring plate 37. This image on monitoring plate 37 can be observed or monitored in enlarged size by binocular microscope 12 having an eyepiece 38.

Another portion of the back-scattered laser beam is reflected on a mirror surface 34a of beam splitter 34 to reach a photomultiplier 42 through a converging lens 39, a mirror 40 and a stop 41 arranged on an optical axis X4. As is well known, the output signal from photomultiplier 42 is analyzed by a correlator (not shown) to determine how the intensity of laser beam back-scattered by the protein particles at spot P fluctuates in time in order to calculate the diameter of the protein particles.

In the monitoring or adjusting mode, light source 25 is first turned on to produce light, which converges on slit 27 through lens 26 and passes therethrough to the mirror 28. The slit light reflected on mirror 28 passes through semitransparent mirror 33 and falls onto collimating lens 29 for reflection on movable mirror 30. The slit light reflected on mirror 30 is focussed by lens 22 on a portion including selected spot P in the lens of the eye to form a slit image thereon.

The light source 31 is then turned on to illuminate pinhole 32 which is focussed at spot P to be measured in conjugate relation to pinhole 32. This spot image by pinhole 32 is illuminated by the above-mentioned slit image, thereby making identification of spot P easy.

The slit image and spot image can be monitored through eyepiece 38 on optical axis X3 arranged at a certain angle relative to optical axis X1. The angle of illumination, that is, optical axis X1 as well as the monitoring angle, that is, optical axis X3 can be adjusted to find the most suitable position in which spot P can be best monitored and measured.

Movable mirror 30 is then moved out of the optical path X1 in the direction A and the laser is activated to produce laser beam L.

Laser beam L is once converged by lens 20 and then caused to fall onto collimating lens 21 to produce collimated light, which is focussed by focussing lens 22 on the same spot as spot P on which the pinhole image is formed.

The light reflected and back-scattered at spot P partially passes through beam splitter 34, objective lens 35 and focussing lens 36 to eyepiece 38 for monitoring and a part of back-scattered light is reflected on the surface 34a of beam splitter 34 to photomultiplier 42 for ophthalmic disease detection.

Figure 3:
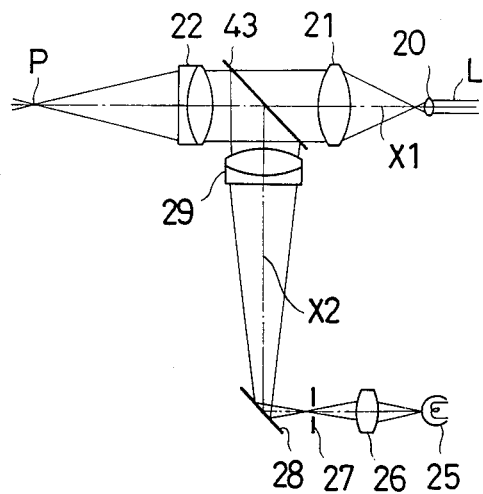
FIG. 3 is a schematic view showing another embodiment of the optical arrangement of the present invention.

FIG. 3 shows another embodiment of the apparatus according to the present invention, in which movable mirror 30 in the first embodiment as shown in FIG. 2 is replaced by a semitransparent mirror or wavelength divider 43 disposed between collimating lens 21 and focussing lens 22 and in which the optical arrangement including light source 31, pinhole 32 and semitransparent mirror 33 is eliminated.

With such an arrangement, light source 25 is turned on as in the first embodiment to produce slit light which is in turn focussed on spot P in the patient's eye to illuminate spot P to be measured and its adjacent portion. The laser is then activated to produce laser beam L, which passes through lenses 20, 21 and semitransparent mirror 43 to lens 22 for focussing on spot P. The amount of light passing through semitransparent mirror 43 to focussing lens 22 can be adjusted by determining the transmission factor of semitransparent mirror or wavelength divider 43. This allows the light falling onto spot P in the lens of the eye to be reduced so little as to be able to avoid discomfort to the patient, but enough for monitoring to identify the spots to be measured. It is also to be noted that the reflection factor of wavelength divider 43, if used instead of the semitransparent mirror, is so determined that light having a predetermined wavelength of slit light from light source 25 can be reflected best thereon and the laser beam is, on the other hand, caused to pass therethrough in a limited amount as mentioned above.

After adjustment of the optimal monitoring angle, the mode is changed into a detection mode in which the back-scattered light is measured for ophthalmic disease analysis. If insufficient amount of back-scattered light occurs, the laser is powered up to increase the light reflected and backscattered at spot P in the lens of the eye.

Figure 4:
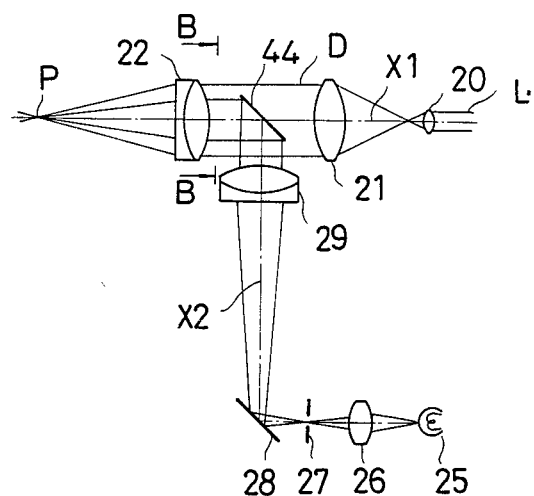
FIG. 4 is a schematic view showing another embodiment of the optical arrangement of the present invention.
Figure 5:
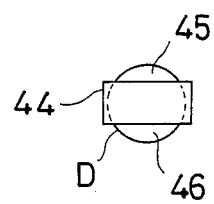
FIG. 5 is a front view showing the position of a movable mirror relative to a focussing lens in FIG. 4.

FIGS. 4 and 5 show another embodiment of an apparatus according to the present invention, in which a movable mirror 44 is disposed between collimating lens 21 and focussing lens 22 so that gaps 45 and 46 can be defined between mirror 44 and the collimated laser beam to cause a portion thereof to pass through movable mirror 44 to focussing lens 22. Mirror 44 is movable between a monitoring mode position as shown in FIG. 4 in which the slit light is reflected thereon and a part of laser beam D passes through gaps 45 and 46 to focussing lens 22, and a detection mode position in which mirror 44 is moved out of the optical path X1 to allow all of laser beam D to pass therethrough.

For the adjustment of the monitoring angle at the beginning of the measurement, light source 25 is turned on to produce the slit light which is reflected on movable mirror 44 and focussed at spot P of the patient's eye. The laser is also activated to produce laser beam D which passes through gaps 45 and 46 and is focussed at spot P illuminated by the slit image formed by the focussed slit light. It is to be noted that gaps 45 and 46 are great enough to allow the passing laser beam D to spot P for monitoring.

In the detection mode, mirror 44 is moved out of optical path X1 to allow the total amount of laser beam D to be focussed at spot P in the lens of the eye to be measured.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention should not be limited to the particular embodiment disclosed as the best mode contemplated for carrying out the invention, but that the invention will include all embodiments falling within the scope of the appended claims.

We claim:

1. An apparatus for detecting ophthalmic disease in the lens of a patient's eye comprising:

a laser for producing a laser beam along an optical path;

slit means having a light source for illuminating said slit means to produce slit light;

reflector means located along said optical path which blocks at least a portion but not all of said laser beam so that said slit light can be used to focus said laser beam on a selected spot while the portion of the laser beam which passes said reflector means is used for monitoring; and, means for moving said reflector means out of said optical path so that all of said laser beam is directed to said selected spot.

2. An apparatus for detecting ophthalmic disease in the lens of a patient's eye comprising:

a laser for producing a laser beam;

means for directing said laser beam along an optical path to a lens of the patient's eye and means for focusing said laser beam at a selected spot in the lens of said patient's eye;

a slit means;

a light source offset from said optical path for illuminating said slit means to produce slit light;

reflector means along said optical path for directing said slit light at substantially the same direction relative to the perpendicular viewing axis of the lens of the patient's eye as said laser beam and means for focusing said slit light at said spot in the lens of said patient's eye to thereby illuminate said selected spot and its adjacent portion at which said laser beam is to be focused; and, said reflector means blocking at least a portion of said laser beam while said slit light is directed to said lens of said patient's eye and means for moving said reflector means so that all of said laser beam is directed to said spot.

* * * * *